United States Patent [19]

Yip

[11] Patent Number: 4,908,432

[45] Date of Patent: Mar. 13, 1990

[54] NOVEL POLYPEPTIDE HAVING GAMMA-INTERFERON ACTIVITY

[75] Inventor: Yum K. Yip, Forest Hills, N.Y.

[73] Assignee: New York University, New York, N.Y.

[21] Appl. No.: 1,786

[22] Filed: Jan. 9, 1987

[51] Int. Cl.⁴ ...................... C07K 15/26; C07K 13/00; A61K 45/02; C12P 21/00
[52] U.S. Cl. .................................. 530/351; 424/85.5; 435/70.5
[58] Field of Search ............... 530/351, 412; 424/85.5, 424/85.4; 435/68, 70

[56] References Cited

U.S. PATENT DOCUMENTS

| | | | |
|---|---|---|---|
| 4,382,027 | 5/1983 | Braude | 424/85.5 |
| 4,617,378 | 10/1986 | Rubinstein | 424/85.5 |
| 4,751,078 | 6/1988 | Nagaghushan et al. | 424/85.5 |

OTHER PUBLICATIONS

Yip et al., Proc. Natl. Acad. Sci., vol. 78, pp. 1601–1605, 1981.

*Primary Examiner*—Blondel Hazel
*Attorney, Agent, or Firm*—Darby & Darby

[57] ABSTRACT

The present invention provides a peptide having an amino acid sequence of less than about 100 amino acids, immunochemically reactive with an antibody directed against human gamma-interferon, and displaying gamma-interferon antiviral and cytolytic activities.

11 Claims, 10 Drawing Sheets

NOVEL POLYPEPTIDE HAVING GAMMA-INTERFERON ACTIVITY

FIELD OF THE INVENTION

This invention relates to novel polypeptides having gamma-interferon activity but a molecular weight substantially lower than that of gamma-interferon.

BACKGROUND OF THE INVENTION

Interferons are a family of inducible, antiviral proteins that are secreted by most animal cells in response to a wide variety of viral and non-viral agents. Interferons have a direct role in antiviral defense in mammals, including humans. They also have been shown to possess immunoregulatory activities and to affect cellular growth. Because of these properties, interferons are currently being tested in the treatment of cancer and immune dysfunctions.

Three distinct major species of interferons have been characterized. Alpha-, or leucocyte interferons are the major species produced by incubating viruses with cells of lymphoid origin. Beta- or fibroblast interferons are the major species produced by nonlymphoid cells upon induction with viral or non-viral agents. Gamma- or immune or type II interferons are the major species produced by lymphocytes (T cells in particular) upon treatment with mitogens, or by sensitized lymphocytes upon treatment with specific antigens.

The three interferon species have very different amino acid sequences and can be distinguished by their physicochemical properties or by specific antisera. For example, antialpha serum does not inhibit the activity of beta- or gamma-interferons.

One of the problems in the clinical application of interferons is that they are in short supply. Purification of native interferons is a complex and expensive procedure. Resolution is often poor and yields are low. Moreover, interferons do not respond well to manipulation (such as that required to purify them) and can be easily inactivated.

Synthetic techniques using either recombinant DNA methods or solid phase peptide synthesis have increased the availability of interferons. However, the recombinant DNA products also need substantial purification (similar to that required for the native products and presenting similar problems) and the peptide-synthesis products are expensive to manufacture because their amino acid chain is quite long (146 amino acids for gamma-interferon).

Therefore, there is a felt need in the art for a peptide having gamma-interferon activity and an amino acid sequence substantially shorter than that of native or recombinant gamma-interferon. Such a peptide could be easily synthesized by solid phase synthesis techniques well-known in the art.

Virtually nothing is known about the existence of biologically active peptide fragments of human gamma-interferon having substantially lower molecular weights. U.S. Pat. No. 4,599,306, issued to Altrock, disclosed a nonadecapeptide whose amino acid sequence duplicated the last 19 amino acid residues of the carboxy terminal of gamma-interferon. However, the peptide was used only to demonstrate and quantitate the binding of a monoclonal antibody to gamma-interferon, and no disclosure was made concerning the biological activities of this peptide.

Rinderknecht et al (*J. Biol. Chem.* 259:6790–6797, 1984) disclosed that removal of up to 16 amino acids from the carboxyl terminal of gamma-interferon did not affect its biological activity. However, no peptide having less than the remaining 130 amino acids but still retaining biological activities was disclosed.

U.S. Pat. No. 4,604,284, issued to Kung et al, disclosed an active 15 kD fragment of gamma-interferon. Kung et al observed that purified gamma-interferon preparations are not homogeneous, but contained a variety of fragments. This 15 kD gamma-interferon fragment resulted from the removal of C-terminal amino acid residues 132–146 by proteases present in the interferon-containing supernatant. However, no active peptide containing less than 131 amino acid residues was disclosed or suggested.

The present inventor has unexpectedly found a novel peptide having gamma-interferon activity and comprising a sequence of less than about 100 amino acids. More particularly, the present inventor has isolated a novel peptide which has a molecular weight of between about 7,000 and 8,000 Daltons, is immunochemically reactive with gamma-interferon antibodies, and displays antiviral and cytolytic activities. Surprisingly, the novel gamma-interferon peptide of the present invention was not detectable on sodium dodecylsulfate polyacrylamide gel electrophoresis (SDS-PAGE), i.e., under denaturing conditions. On SDS-PAGE, only two gamma-interferon polypeptides were detectable with apparent molecular weights of 52 kD and 28 kD.

The use of the process for purifying the peptide of the present invention, wherein high resolution and speed in the separation of protein molecules was achieved, coupled with the high degree of recovery of biologically-active interferon molecules, allowed for the discovery of this heretofore unrecognized component of the gamma-interferon-containing supernatant.

The present invention has several objects including, but not limited to, the following:

To isolate and characterize a substantially smaller novel polypeptide having gamma-interferon activities;

To purify this peptide without substantially decreasing its activity;

To isolate and characterize a novel polypeptide having gamma-interferon activities that could be produced conveniently by recombinant DNA or synthetic organic techniques;

These and other objects of the present invention will be apparent to those skilled in the art in light of the present descriptions, accompanying claims, and appended drawings.

SUMMARY OF THE INVENTION

The present invention provides a peptide which has a molecular weight substantially lower than gamma-interferon or known polypeptides displaying gamma-interferon activity, and is immunochemically reactive with gamma-interferon antibodies. This novel gamma-interferon species displays antiviral and cytolytic activities similar to classical gamma-interferon.

In another aspect, the present invention provides a process for purifying both the novel and classical gamma-interferon peptides. The process comprises sequential chromatography using silicic acid, an anion exchange resin (run under conditions whereby the novel and classical gamma-interferon species are excluded), high-separation speed molecular-sieve chromatography under non-denaturing conditions, and a cation exchange resin column.

DETAILED DESCRIPTION OF THE INVENTION

Figure 1:
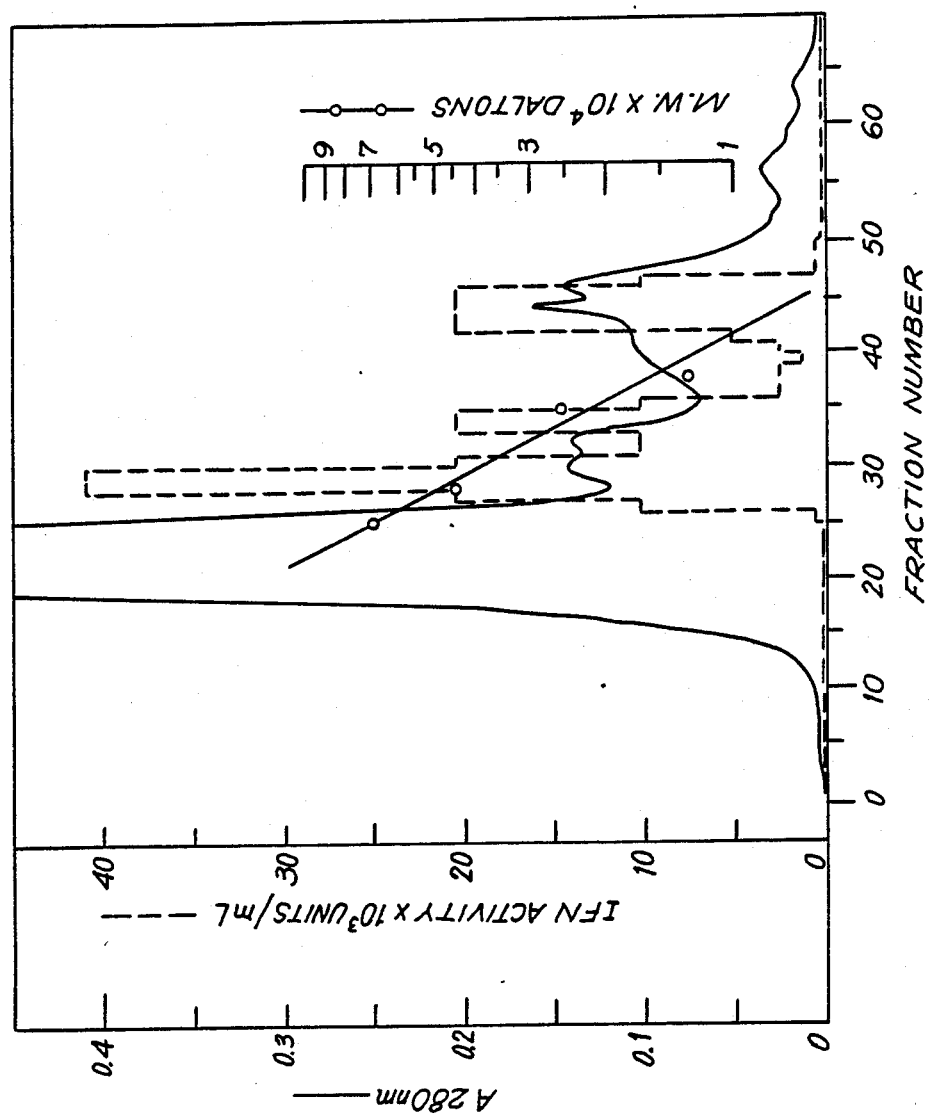
FIG. 1 is a graph of the elution profile of proteins and interferon activity from a high-separation speed molecular-sieve column.

The present inventor has identified and isolated a novel biologically active peptide displaying gama-interferon activities. It is believed that this peptide (hereinafter referred to as novel gamma-interferon) is a sub-species of gamma-interferon. This classification is based on the complete neutralization of the antiviral activity of this protein by monoclonal specific for the well-established human gamma-interantibodies feron (hereinafter referred to as classical gamma-interferon).

Natural human gamma-interferon is believed to be encoded by a single gene, and the protein is believed to exist in the native state in the form of a dimer. It has an apparent molecular weight of about 58,000 Daltons (58 kD) as determined by conventional molecular-sieve chromatography under nondenaturing conditions. Molecular weight determination by sodium dodecylsulfate polyacrylamide gel electrophoresis (SDS-PAGE) has shown that human gamma-interferon can be resolved in two major components with apparent molecular weights of 25 kD and 20 kD, respectively. The differences in the molecular weights of the heretofore known human gamma-interferon subspecies are believed to represent differences in the degree of glycosylation, i.e., complete or partial glycosylation at the two N-linked glycosylation sites.

A characteristic that distinguishes this novel gamma-interferon species from the classical ones is its size. Novel gamma-interferon of the present invention is substantially smaller (i.e. has a substantially lower molecular weight) than classical gamma-interferon and either of the 25 kD add 20 kD components thereof. As used herein, substantially smaller than gamma-interferon is defined as less than about 10,000 Daltons, corresponding to an amino acid sequence length of less than 100 amino acids. Size estimation by molecular-sieve chromatography under non-denaturing condition indicates that the apparent molecular weight of this novel gamma-interferon is between 7,000–8,000 Daltons. Using 115 as the mean residue weight for the amino acids, novel gamma-interferon is calculated to contain less than 70 amino acids; this is an upper estimate since the peptide also contains carbohydrates (see Example 3 below). Surprisingly, on sodium dodecylsulfate polyacrylamide gel electrophoresis (SDS-PAGE), novel gamma-interferon of the present invention resolves into a major and a minor component with molecular weight estimates of about 52 kD and 28 kD, respectively.

The novel gamma-interferon was first identified when using molecular-sieve chromatography under non-denaturing conditions using a High Performance Liquid Chromatograph (HPLC), specifically the FAST PROTEIN LIQUID CHROMATOGRAPH, (FPLC, Pharmacia, Piscataway, N.J.) for the purification of gamma-interferon. Consistent with the above-mentioned classification of this peptide as a gamma-interferon species, novel gamma-interferon was also found to exhibit direct cytolytic activity on tumor cells as well as the ability to activate monocytes exerting cytotoxic activity on tumor cells, both properties of gamma-interferon.

This heretofore unrecognized natural form of gamma-interferon can be obtained from gamma-interferon-containing solutions, including but not limited to, culture media of human peripheral blood leukocytes (PBL) stimulated with a combination of a diterpene phorbol ester (such as 12-0-tetradeconylphorbol-13-acetate, TPA) and the T cell mitogen phytohemagglutinin (PHA)

A preferred sequential chromatographic procedure for the purification of the present gamma-interferon (and/or its separation from larger gamma-interferon subspecies and components) comprises the steps of:
(1) adsorption of gamma-interferon on silicic acid;
(2) adsorptive removal of some of the contaminating proteins on an anion exchange residue;
(3) high-separation speed molecular-sieve chromatography, and
(4) cation-exchange chromatography.

The first step in the purification procedure involves adsorption of a gamma-interferon-containing solution containing classical and novel gamma-interferon onto silicic acid. This can be accomplished using a column format, or preferably by a batch method. After adsorption, the silicic acid is washed with a neutral buffer, such as phosphate buffered saline (PBS), in order to remove unbound proteins. The bound material (containing both novel and classical gamma-interferons) is eluted using PBS containing 50% (vol./vol.) of a suitable solvent as the eluant. Suitable solvents include, but are not limited to, nonionic hydroxylated compounds such as glycerol, propylene glycol, polyethylene glycol or preferably, ethylene glycol.

The silicic acid eluate is further purified by adsorptive removal of contaminating proteins on an anion exchange residue, such as DEAE (DEAE-SEPHACEL, Pharmacia Fine Chemical Co., Piscataway, N.J.) using a column format, or preferably, by a batch method. The anion exchanger is equilibrated to pH 7.7, thereby causing non-gamma interferon contaminants to bind, whereas classical gamma-interferon (with an isoelectric point (pI) of 8.5) and novel gamma-interferon (with an expected pI of greater than 8.5) remain (are excluded) in the unbound effluent.

The anion exchange unbound supernatant is then subjected to high-separation speed molecular sieve chromatography under non-denaturing conditions. Non-denaturing conditions are defined as lacking denaturants, such as sodium dodecylsulfate or denaturing treatments, such as heating, which break up nonconvalent interactions. A high-speed separation technique is employed in conjunction with the molecular sieve column. High speed is achieved by the application of increased pressure on the column and the use of chromatography media which can withstand the pressure. A High Performance Liquid Chromatograph (HPLC) is preferably employed which is compatible with biological substances (FPLC, Pharmacia Fine Chemicals, Piscataway, N.J.). Most preferably, a SUPEROSE 12 column (Pharmacia Fine Chemicals, Piscataway, N.J.) (run under conditions described below) is employed. The only requirements of this column are that it can resolve peptides in the molecular weight range of the peptides of the present invention and that it can be run under the increased pressure needed to ensure a fast completion of this step. Samples are concentrated to a small volume, using standard techniques such as membrane dialysis or, preferably, dialysis using the powdered sodium salt of carboxymethyl cellulose, as is well-known in the art. The samples are applied to the column, eluted, and the fractions containing gamma-interferon are identified by antiviral activity as detailed below. Novel gamma interferon resolves in fractions corresponding to the 7,000 to 8,000 Dalton region, whereas classical gamma-interferon resolves in the 50,000 region (presumably due to aggregation of the subunits under the non-denaturing conditions employed).

The novel gamma-interferon-containing eluate from the molecular sieve chromatography step above is then purified by cation-exchange chromatography. Suitable columns include carboxymethyl cellulose (Whatman Laboratory Products, Clifton, N.J.), CM-SEPHADEX (Pharmacia Fine Chemical Co., Piscataway, N.J.) and preferably MONO S (Pharmacia Fine Chemicals, Piscataway, N.J.) Fractions corresponding to the 8,000 Dalton region, containing novel gamma-interferon, are bound in the presence of a buffer, preferably Tris HCl, pH 7.5 and eluted using a linear gradient composed of the buffer plus a suitable salt, preferably sodium chloride (1 molar). Fractions containing novel gamma-interferon are identified by assaying for antiviral activity or by radioimmunoassay, the latter described in Example 4 below.

The key experimental approach that allowed for the identification of the novel gamma-interferon of the present invention was the use of a high-separation speed molecular-sieve chromatography technique, preferably using HPLC. Chromatography on the HPLC systems affords high resolution and speed in the separation of protein molecules. Completion of an HPLC/molecular-sieve chromatography experiment can be achieved in less than one hour, whereas a similar experiment using conventional techniques (e.g., flow control by gravity or a peristaltic pump) would require more than ten hours for completion. An important determinant in the purification process is the speed at which the molecular-sieve chromatography step is carried out. In a preferred embodiment of the process, a highly crosslinked agarose column (SUPEROSE 12, Pharmacia Fine Chemicals, Piscataway, N.J.) is employed to separate proteins.

When used under HPLC conditions, a constant pressure of at least about 125 lbs. per square inch, and preferably about 225 lbs. per square inch is maintained. The maximum pressure that can be used in this process is a function of the materials and equipment employed. For example, the cross-linked agarose of the preferred embodiment can withstand up to about 430 lbs. per square inch. Therefore, the entire chromatographic separation can be completed in about two hours, and preferably in less than one hour.

Figure 8:
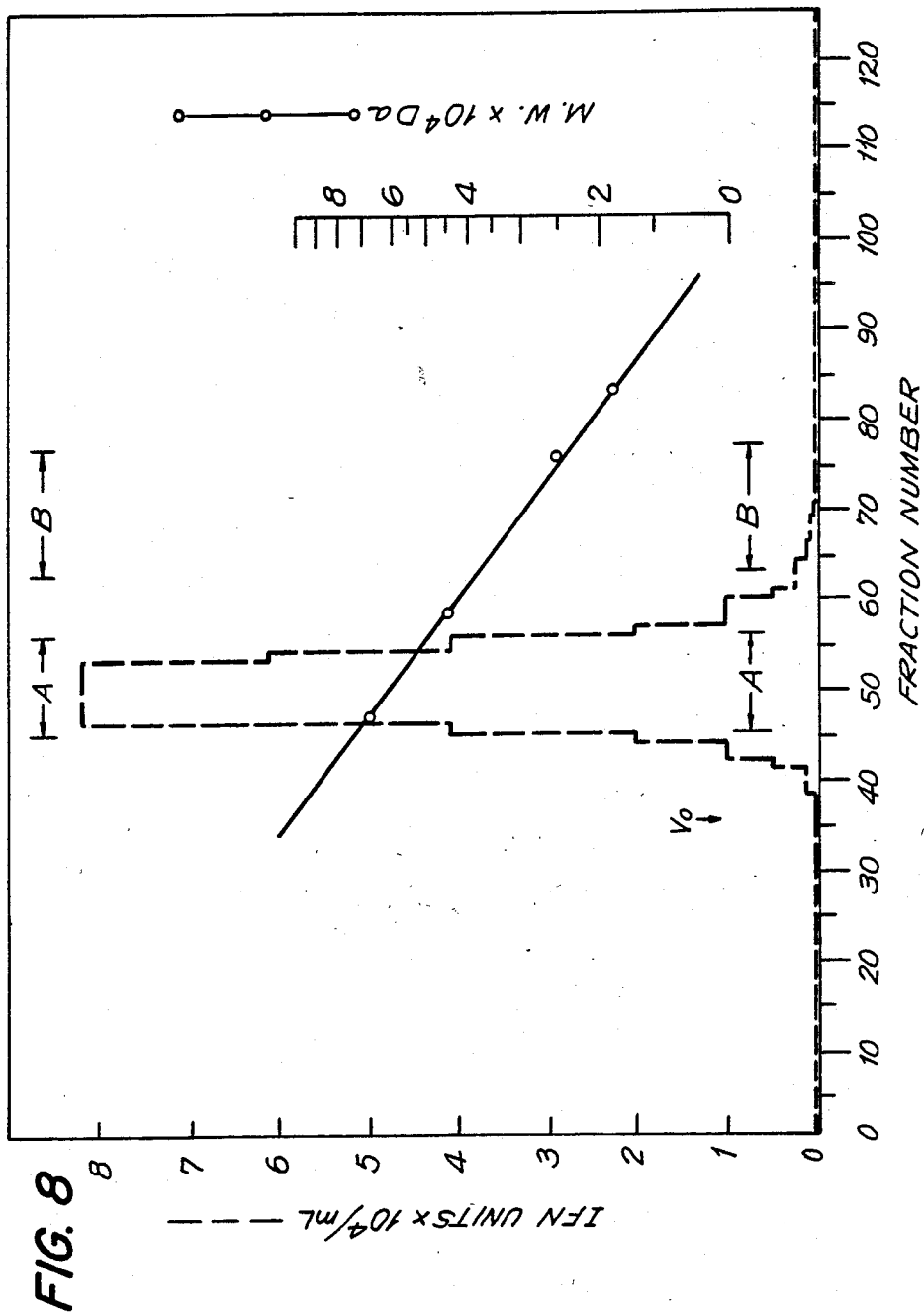
FIG. 8 is a graph of the elution profile of a gamma-interferon-containing solution from a conventional molecular sieve column.

Subsequent to the discovery of novel gamma-interferon, the elution profile of gamma-interferon by conventional molecular-sieve chromatography on a conventional molecular sieve column (BIO-GEL P-200, Bio-Rad Laboratories, Richmond, Calif.) was re-examined. The elution profile, as shown in FIG. 8, is consistent with that previously reported; the antiviral activity was recovered essentially in one broad symmetrical elution peak with an estimated molecular weight of 60 kD (an estimated molecular weight of 58 kD was reported by Yip, Y.K. et al (1981) Proc. Natl. Acad. Sci. U.S.A. 78:1601-1605). A sample of the same gamma-interferon preparation chromatographed on a HPLC/molecular-sieve column was resolved into a 50 kD, a 14.5 kD, and a 8 kD component as shown in FIG. 1.

Figure 9:
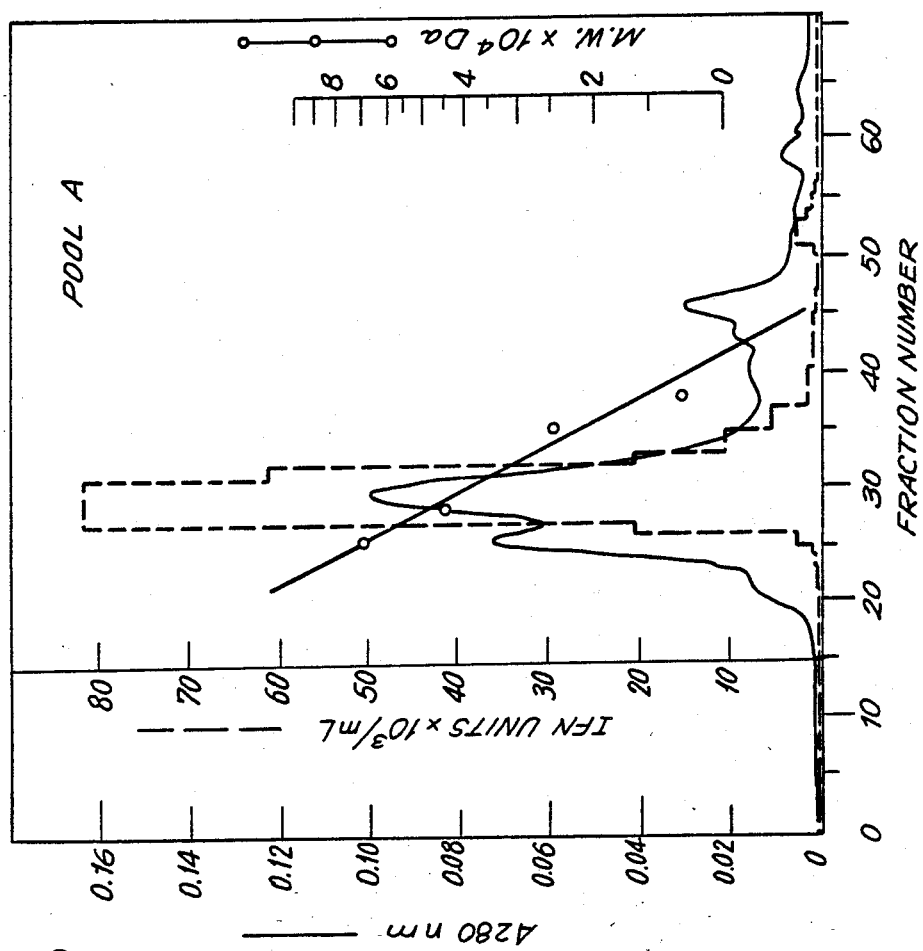
FIG. 9 is a graph of the elution profile of the gamma-interferon-containing solution isolated from the region marked A of FIG. 8 when re-chromatographed using HPLC.
Figure 10:
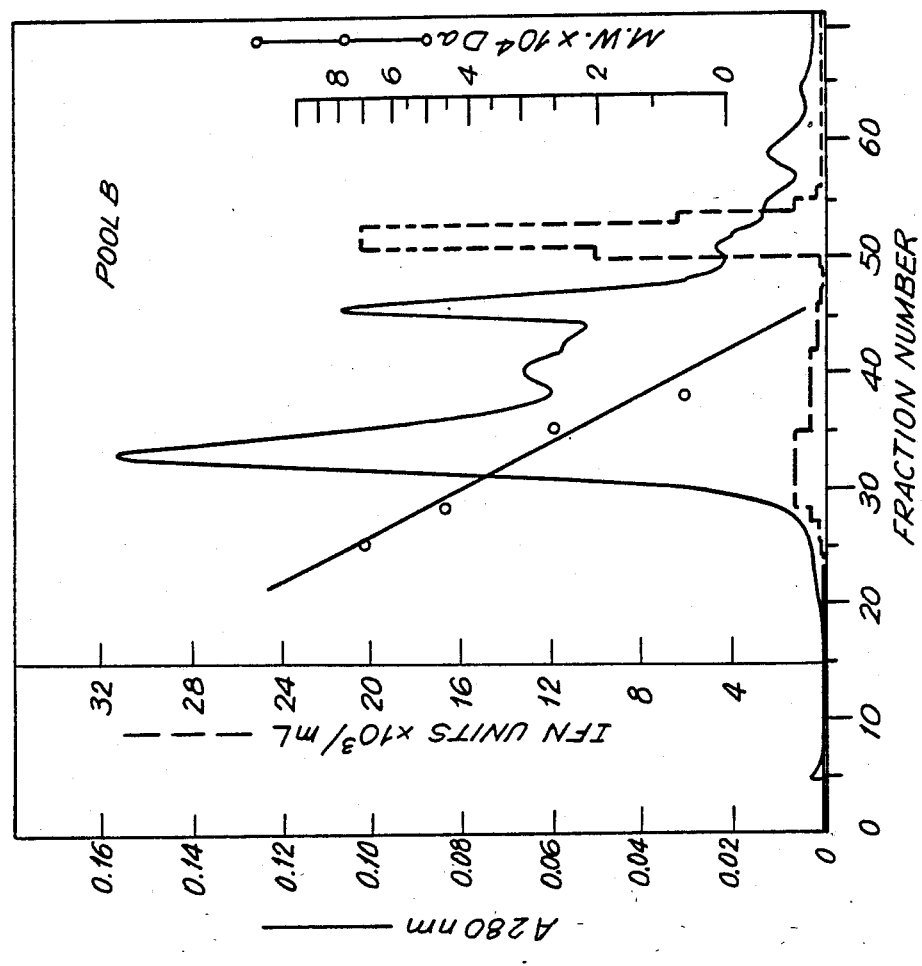
FIG. 10 is a graph of the elution profile of gamma-interferon-containing solution isolated from the region marked B in FIG. 8 when re-chromatographed using HPLC.

The peak portion (marked A in FIG. 8) and the trailing portion (marked B in FIG. 8) eluted from the molecular-sieve chromatography experiment were pooled separately and concentrated by dialysis using the powdered sodium salt of carboxymethyl cellulose (AQUACIDE II, Calbiochem, San Diego, Calif.) and each was then further analyzed by HPLC/molecular-sieve chromatography on a highly crosslinked agarose (SUPEROSE 12, Pharmacia, Fine Chemicals, Piscataway, N.J.) column. Results summarized in FIGS. 9 and 10 show that the pool from the peak portion (Pool A, FIG. 8) consists essentially of classical gamma-interferon while the pool from the trailing portion (Pool B, FIG. 8) consists essentially of novel gamma-interferon. The contrasting results presented in FIGS. 1, 8, 9 and 10 sieve column chromatography to separate the classical from the novel species of gamma-interferon. Diffusion of the interferon molecules during the extended period of time in performing conventional molecular-sieve chromatography apparently further compromises the already poor resolution obtainable with this conventional technique.

The four step chromatographic procedure presented above is also suitable for purifying classical gamma-interferon obtained from any source. The only deviations from the above procedure are that the fractions containing classical gamma-interferon obtained from the molecular sieve chromatography step (Step 3 above), corresponding to the 50,000 Dalton region, are applied to and eluted from a cation exchange resin.

The purification procedure leads to a substantial purification of both classical and novel gamma interferons. Little antiviral activity is lost or inactivated using this method. An exact determination of the degree of purification could not be quantitated due to the small amount of protein present in the samples. However, analysis of this material by SDS-PAGE (see FIG. 3, lane 4) demonstrated that the novel gamma-interferon of the present invention or aggregates thereof is the major (greater than 95%) stainable protein component.

The present invention is further described below in the following specific examples, which are intended to illustrate the present invention without limiting its scope.

EXAMPLE 1

Induction of Cell Cultures To Produce Human Gamma-Interferon

Human blood cell concentrates obtained in the form of buffy coats or plateletpheresis residues were used for seeding production cultures. The cell concentrates were diluted in serum-free RPMI 1640 medium (Gibco, Grand Island, N.Y.) containing heparin (40 USP units per ml, Sigma, St. Louis, Mo.) without further processing. Cultures seeded at approximately $6 \times 10^6$ cells per ml at 100 ml per petri dish (150 mm in diameter, Falcon, division of Becton Dickinson, Oxnard, Calif.) were treated with TPA, (5 ng per ml, LC Services, Woburn, Mass.) two hours prior to the addition of PHA (5 microgram per ml, Bouroughs Wellcome, Research Triangle Park, N.C.) as described in Vilcek, J. and Yip, Y. K., U.S. Pat. No. 4,460,685 incorporated herein by reference. The culture media were collected after 48–72 hours of incubation at 37° C. in a humidified $CO_2$ incubator, and stored at 4° C. until use. Some culture media used for the isolation of novel gamma-interferon were stored at 4° C for as long as 12 moths.

The results from four different experiments are presented below in Table 1.

TABLE 1

Interferon Activity in Media of TPA/PHA Stimulated PBL Cultures

| Experiment No. | Interferon Titer Units/ml |
|---|---|
| 1 | 10,240 |
| 2 | 20,430 |
| 3 | 15,360 |
| 4 | 20,480 |

Interferon yields from TPA/PHA stimulated PBL cultures as described above are consistent with results reported previously (Yip, Y. K. et al. Infect. Immun., 34:131–139, 1981).

EXAMPLE 2

Purification of the Novel Gamma-Interferon

The efficacy of each of the chromatographic steps in the purification scheme was monitored with respect to the recovery of antiviral activity; protein recovery was not measured except for the anion exchange step.

Step 1. Adsorption of Gamma-Interferon On Silicic Acid

The first step in the purification procedure is adsorption of a solution containing novel and classical gamma-interferon onto silicic acid beads (Mallinckrodt, St. Louis, Mo.), by a batch method. Silicic acid beads were added to the gamma-interferon-containing culture fluid at a ratio of 1:40 (vol./vol.), and the mixture was allowed to rotate at approximately 40 rpm on a roller apparatus (Bellco, Philadelphia, Pa.) at 4° C. After overnight adsorption, the silicic acid beads with bound gamma-interferons were collected by centrifugation, and washed three times each with three volumes of phosphate-buffered saline (PBS, pH 7.4/0.15 M NaCl) to remove unbound proteins. Gamma-interferons were then eluted from the silicic acid beads with three volumes of 50% (vol./vol.) ethylene glycol in PBS. The presence of gamma-interferons in the eluted fractions was determined by a biological assay based on the well-known interferon-mediated inhibition of the cytopathic effect of encephalomyocarditis virus in human foreskin fibroblast cells (FS-4) (hereinafter referred to as antiviral activity) as described by Havell, E. A. et al., Antimicrob. Ao. Chemother. 476:484, 1982, incorporated by reference. Examples of interferon activity recovery from silicic acid chromatography are listed in Table 2 below.

TABLE 2

Recovery of Interferon Activity on Silicic Acid Adsorption Chromatography

| | Interferon Units $\times 10^3$ | | |
|---|---|---|---|
| Experiment No. | Starting | Flow-Through | Eluted |
| 1 | 10,240 | 128 (1.25%)* | 5,280 (52%) |
| 2 | 20,480 | 256 (1.25%) | 20,736 (101%) |
| 3 | 15,360 | 256 (1.66%) | 17,088 (110%) |
| 4 | 20,480 | 128 (0.62%) | 18,944 (93%) |

*Recovery of interferon activity expressed as percent of the starting titer.

Step 2. Adsorptive Removal of Contaminating Proteins Using Anion Exchanger Beads The gamma-interferon-containing eluate from the silicic acid step was equilibrated to 25 mM sodium phosphate at pH 7.7 by exhaustive dialysis. The resulting gamma-interferon sample was then purified further by absorptive removal of contaminating proteins on anion exchanger beads (DEAE-SEPHACEL beads, Pharmacia Fine Chemicals, Piscataway, N.J.) by a batch method. The beads were equilibrated to 25 mM sodium phosphate at pH 7.7, added to the gamma-interferon sample at a ratio of 1:100 (vol./vol.) and allowed to mix overnight as described for the silicic acid step. Classical and novel human gamma-interferons, which have isoelectric points (pI) greater than 8.5, will not bind to the anionic-exchanger beads at pH 7.7 while most other proteins known to have pI's at or below 7.7 will be removed from the sample solution by adsorption onto the beads. The beads were then removed by centrifugation, and the gamma-interferon-containing supernatant was concentrated to approximately one-tenth of the starting volume in a dialysis bag with a molecular weight cutoff at 2,000 D by dehydration on a bed of the powdered sodium salt of carboxymethyl cellulose (AQUACIDE II, Calbiochem, San Diego, Calif.). Examples of interferon activity recovered from this step are listed in Table 3 below.

TABLE 3

Recovery of Interferon Activity and Proteins From Anion Exchange Chromatography

| Experiment no. | Interferon units/ml[a] | | $A_{280 \, nm}$ | |
|---|---|---|---|---|
| | Before adsorption | After adsorption | Before adsorption | After adsorption |
| 1 | 25,600 | 19,200 (75%)[b] | 1.994 | 0.144 (7.2%)[c] |
| 2 | 30,720 | 30,720 (100%) | 0.225 | 0.032 (14.2%) |
| 3 | 3,840 | 1,920 (50%) | 0.037 | 0.005 (13.5%) |

[a] Interferon samples used in these experiments were partially purified by chromatography on silicic acid beads.
[b] Recovery expressed as percent of starting titer.
[c] Recovery expressed as percent of starting absorbance.

The above data demonstrate that the majority of antiviral activity is recoverable in the non-bound fraction, while greater than 85% of the non-interferon protein contaminants are removed in this step.

Step 3. Molecular-Sieve Chromatography

Molecular-Sieve Chromatography was carried out under non-denaturing condition. A highly crosslinked agarose column, 10×300 mm, (SUPEROSE 12, Pharmacia Fine Chemicals, Piscataway, N.J.) with a resolution range of $10^3$ to $3 \times 10^5$ D in molecular weight was equilibrated by washing with 5 column volumes of PBS. The column was calibrated with the use of bovine serum albumin (68,000), ovalbumin (45,000), chymotrypsinogen A (25,000), and cytochrome C (12,700). Gamma-interferon samples purified by chromatography on silicic acid beads and anion exchanger were concentrated by dehydration. Samples in a volume of 200 microliters were applied to the column and eluted with PBS. The flow-rate of the elution buffer was regulated at 0.5 ml per minute by an HPLC controller (FPLC, Pharmacia Fine Chemicals, Piscataway, N.J.) under a pressure of 225 lbs. per square inch. Fractions of 0.25 ml each were collected. Examples of interferon activity recovered from this step are listed in Table 4 below.

TABLE 4

Recovery of Interferon Activity From HPLC Molecular-Sieve Chromatography

| Experiment No. | Interferon Units | | |
|---|---|---|---|
| | Starting | Classical Species | Novel Species | Total Recovery |
| 1 | 307,200 | 100,260 (77%)[a] | 30,100 (23%)[a] | 130,360 (42%)[b] |
| 2 | 81,920 | 78,480 (76%) | 25,440 (24%) | 103,920 (126%) |
| 3 | 163,840 | 116,740 (84%) | 22,340 (16%) | 139,080 (85%) |
| 4 | 163,840 | 140,540 (81%) | 32,400 (19%) | 172,940 (106%) |

[a]Recovery of interferon activity in elution volumes corresponding to the classical (50 kD) and the novel (8 kD) species expressed as percent of total recovery.
[b]Total recovery of interferon activity expressed as percent of the starting titer.

Step 4. Ion-Exchange Chromatography

A cation-exchange column (MONO S/HR 5/5, Pharmacia, Piscataway, N.J.) was equilibrated to pH 7.5 with 20 mM Tris HCl (buffer A). Fractions corresponding to the 50 kD (classical gamma-interferon) and to the 8 kD (novel gamma-interferon) regions from the molecular sieve column were pooled separately and equilibrated with buffer A by exhaustive dialysis. Purification of each of these interferon species on the column was carried out with a linear NaCl gradient composed of loading buffer (buffer A) and final buffer (buffer A with 1.0 M NaCl), the salt gradient generated by a HPLC controller at a flow-rate of 0.5 ml/min. Fractions of 0.25 ml each were collected. Examples of interferon activity recovered from this step are listed in Table 5 (classical gamma-interferon) and in Table 6 (novel gamma-interferon).

TABLE 5

Recovery of Classical Gamma-Interferon Activity[a] From Ion-Exchange Chromatograhy

| Experiment No. | Interferon Units | | | |
|---|---|---|---|---|
| | Starting | Flow-Through | Eluted | Total Recovery |
| 1 | 81,920 | 21,460 (23%)[b] | 70,080 (77%) | 91,540 (112%)[c] |
| 2 | 40,960 | 12,920 (34%) | 24,740 (66%) | 37,660 (92%) |
| 3 | 102,400 | 19,200 (19%) | 80,230 (81%) | 99,430 (97%) |

TABLE 5-continued

Recovery of Classical Gamma-Interferon Activity[a] From Ion-Exchange Chromatograhy

| Experiment No. | Interferon Units | | | |
|---|---|---|---|---|
| | Starting | Flow-Through | Eluted | Total Recovery |
| 4 | 307,200 | 102,400 (40%) | 105,890 (60%) | 253,290 (82%) |

[a]Interferon activity pooled from HPLC/SUPEROSE 12 (Pharmacia Fine Chemicals, Piscataway, NJ) column fractions corresponding to the 50 kD elution volume.
[b]Recovery of interferon activity in the flow-through and elution fractions expressed as percent of total recovery.
[c]Total recovery of interferon activity expressed as percent of the starting titer.

TABLE 6

Recovery of Novel Gamma-interferon Activity[a] From Ion-Exchange Chromatography

| Experiment No. | Interferon Units | | | |
|---|---|---|---|---|
| | Starting | Flow-Through | Eluted | Total Recovery |
| 1 | 12,800 | 0 | 18,400 (100%)[b] | 18,400 (144%)[c] |
| 2 | 51,200 | 1,600 (4%)[b] | 33,980 (96%) | 35,580 (70%) |
| 3 | 25,600 | 0 | 36,370 (100%) | 36,370 (142%) |
| 4 | 102,400 | 2,800 (5%) | 53,900 (95%) | 56,700 (55%) |

[a]Interferon activity pooled from HPLC/molecular sieve column fractions corresponding to the 8 kD elution volume.
[b]Recovery of interferon activity in the flow-through and elution fractions expressed as percent of total recovery.
[c]Total recovery of interferon activity expressed as percent of the starting titer.

As can be seen from the above results, novel gamma-interferon activity was quantitatively recovered from each of the above steps. It should be noted that there is an inherent 2fold deviation in determining interferon titers using the biological assay (inhibition of viral cytopathic effect) of the present invention. Therefore, some recoveries listed above are greater than 100%.

In addition, novel gamma-interferon quantitatively bound to the ion exchange column (Table 6), whereas classical gamma-interferon showed a larger percentage of material (19–40 %, Table 5) which did not bind. This most likely reflects the more heterogeneous nature of the classical gamma-interferon starting material (i.e., the 50 kD starting material is more heterogeneous in terms of its total net charge than the 8 kD novel gamma-interferon).

EXAMPLE 3

Physicochemical Properties of the Novel Gamma-Interferon

A. Molecular Size Determination Under Non-Denaturing Conditions: Natural human gamma-interferon was resolved into three distinct molecular size components by HPLC/molecular-sieve chromatography under non-denaturing conditions. A typical elution profile of proteins and interferon activity on the highly crosslinked agarose column is shown in FIG. 1. The first activity component was eluted in a volume corresponding to an apparent molecular size of about 50 kD, the second corresponding to about 14.5 kD, and the third corresponding to about 8 kD. The antiviral activity of all three molecular weight species was neutralized specifically by antibodies to gamma-interferon and not by antibodies to alpha-interferon (see Example 4 below).

The identification of the 50 kD component is an expected finding which has been reported by the present inventor. The 14.5 kD gamma-interferon may possibly be a monomeric form of unglycosylated classical gamma-interferon. The existence of the 8 kD novel gamma-interferon of the present invention has never been reported before either with natural or recombinant human gamma-interferon preparations, under non-denaturing or denaturing conditions.

Figure 2:
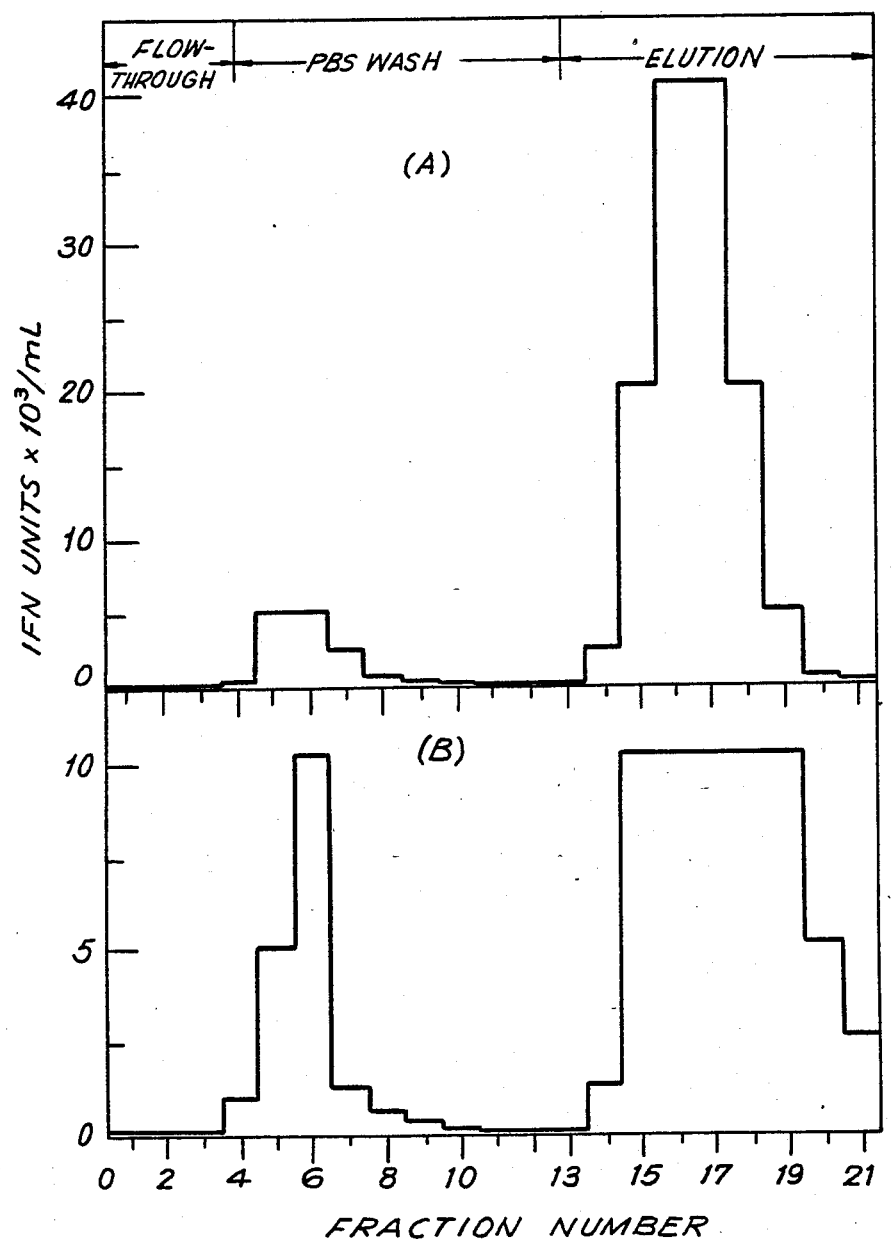
FIG. 2 is a graph of the elution profile of classical (A) and novel (B) gamma-interferon from a ConA column.

B. Determination for the Presence of Carbohydrates in Novel Gamma-Interferon: The 50 kD classical gamma-interferon dissociates into 25 kD and 20 kD subunits on SDS-PAGE. Differences in the molecular size of the 25 kD and 20 kD subunits have been shown to be due to differences in the degree of glycosylation of the polypeptide chain. It was therefore of interest to determine if the unusually small molecular size of the novel gamma-interferon is due, at least in part, to the lack of glycosylation. The presence or absence of carbohydrates was determined by chromatography on a concanavalin A (ConA) column as has been described (Yip, Y.K. et al. *Proc. Natl Acad. Sci. U.S.A.*, 78:1601–1605, 1981). Briefly, classical and novel gamma-interferon isolated by HPLC/molecular-sieve chromatography were each applied to a ConA column (ConA-SEPHAROSE, Pharmacia Fine Chemicals, Piscataway, N.J.). After completion of sample loading, each column was washed with 4 column volumes of PBS. Specifically bound proteins, i.e. those containing carbohydrates, were then eluted with the use of 50 mM sodium phosphate (pH 7.4) containing 0.15M NaCl and 0.2M alpha-methyl-D-mannoside. Typical elution profiles of classical and novel gamma-interferon on ConA columns are shown in FIG. 2.

Recovery of interferon activity from ConA column chromatography is summarized in Table 7 below.

TABLE 7

| Interferon Species | Recovery of Interferon Activity from ConA Column Chromatography | | | |
|---|---|---|---|---|
| | Stapting | Unbound | Bound | Total Recovery |
| Classical | 204,800 | 28,560 (10%)[a] | 263,040 (90%)[a] | 291,600 (142%)[b] |
| Novel | 143,360 | 37,280 (25%) | 110,080 (75%) | 147,360 (102%) |

[a]Expressed as percent in total recovered activity.
[b]Expressed as percent of starting activity.

Complete recovery of the antiviral activity was obtained for both species of interferon. Of the 291,600 units recovered for the classical gamma-interferon, 28,560 units (10%) were recovered in the unbound (flow-through and PBS wash) fraction, the remaining 263,040 units (90%) were recovered by elution with the alpha-methyl-D-mannoside containing buffer. Of the 7,360 units of novel gamma-interferon recovered, 37,280 units (25%) were recovered in the unbound fraction; 110,080 units (75%) were recovered from the bound fraction. Thus, it appears that the majority of the novel gamma-interferon molecules, like those of the classical gamma-interferon, are glycosylated. The unbound activities in both cases were not due to overloading, since both remained unbound when applied to fresh ConA columns.

C. Molecular Size Determination Under Denaturing Condition: An unexpected finding was observed when attempts were made to confirm the molecular weight and to examine the purity of the 4-step purified novel gamma-interferon by SDS-PAGE under reducing condition. Electrophoresis was carried out in 12.5% (w/v) acrylamide slab gels according to the Laemmli procedure (Laemmli, U. K., *Nature*, 227:680, 1970), and the presence of protein bands was determined by the highly sensitive silver-staining procedure (Merril, C. R. et al. *Anal. Biochem.*, 105:361, 1980). Molecular weight markers used in these experiments were phosphorylase B (92,500), bovine serum albumin (68,000), ovalbumin (45,000), carbonic anhydrase (31,000), soybean trypsin inhibitor (21,500), and lysozyme (14,400).

Figure 3:
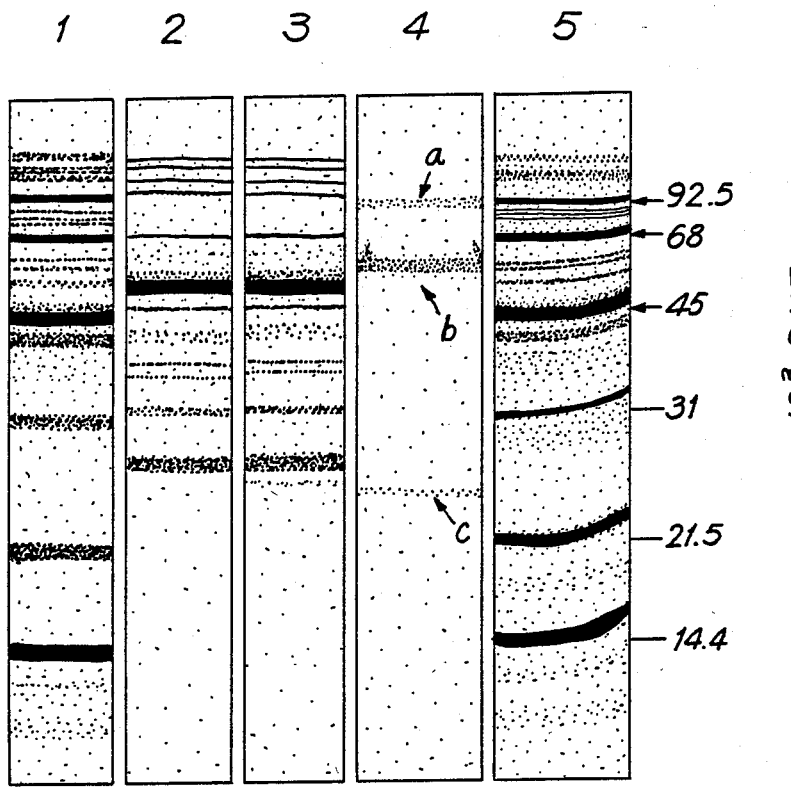
FIG. 3 is an SDS-PAGE gel of the 4-step purified novel gamma-interferon.

The silver stained protein profile of the 4-step purified novel gamma-interferon is shown in FIG. 3, lane 4; lanes 1 and 5 are molecular weight markers; lanes 2 and 3 are duplicates of a preparation of partially purified monoclonal antibodies used here as an additional molecular weight marker in the 50 kD range (the heavy chain of immunoglobulin). One major protein band (band b) which appears to account for greater than 95% of the stainable proteins was observed to have migrated to a distance between the 68 kD and the 45 kD markers (about 52 kD). Two minor protein bands, one (band a) migrated to a distance between the 92.5 kD and the 68 kD markers, and the other (band c) between the 31 kD and the 21.5 kD markers. There is no discernible protein band (below the 14.4 kD marker) that would correspond to the 8 kD novel gamma-interferon. The absence of stainable protein bands around the 8 kD area may either be due to the fact that the amount of the novel gamma-interferon protein applied in this experiment was blow the detection limit of the silver staining technique, or more likely that this novel protein has an anomalous migration behavior on SDS-PAGE.

Figure 4:
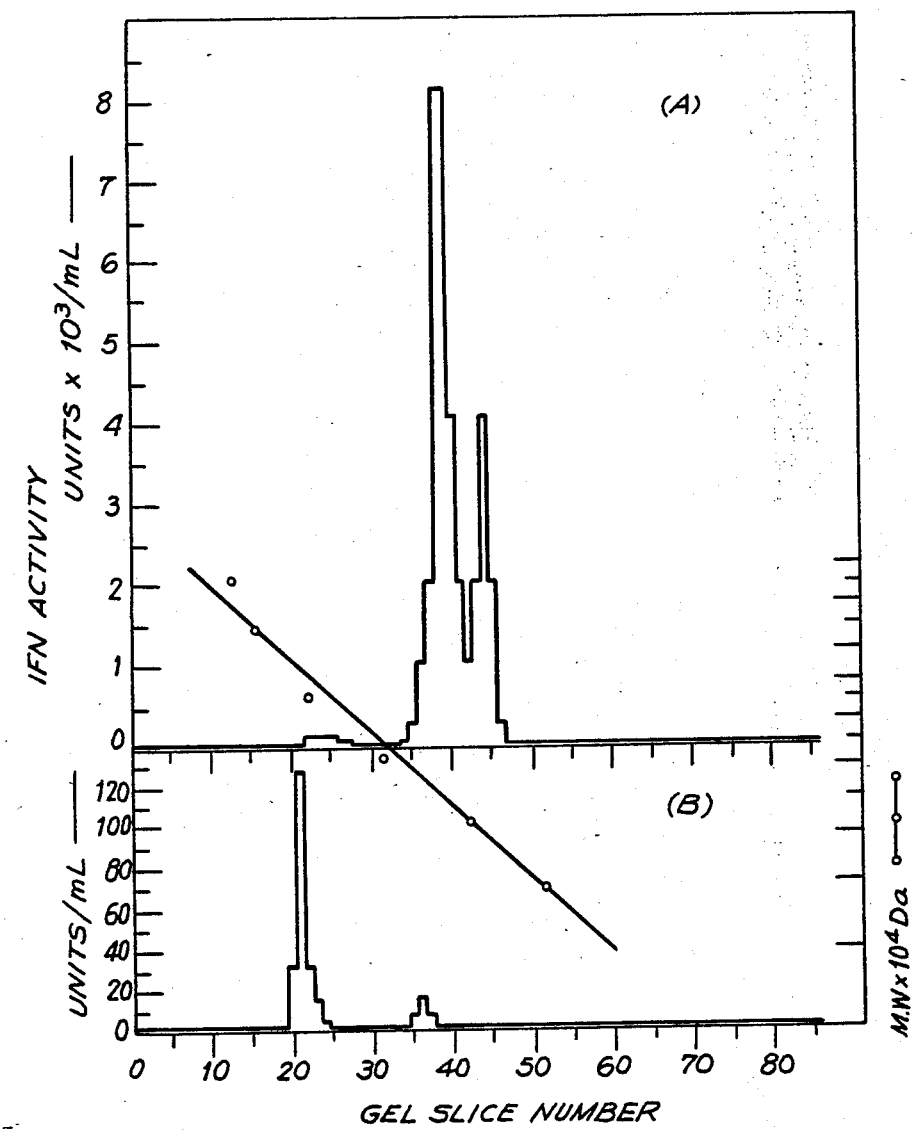
FIG. 4 is a graph of the activity profiles of classical (A) and novel (B) gamma-interferons after SDS-PAGE.

In order to be certain of the identification of the novel gamma-interferon protein on SDS-PAGE, attempts were made to identify it by its antiviral activity. This approach has been described and allowed for the delineation of the subunit composition of classical human gamma-interferon (Yip, Y. K. et al. *Proc. Natl. Acad. Sci. U.S.A.*, 79:1820–1824, 1982). FIG. 4 shows a comparison of the activity profiles of classical (panel A) and novel (panel B) gamma-interferon after SDS-PAGE. It is clear that the activity profiles for these two interferon species are different from each other. Classical gamma-interferon showed the typical 25 kD and 20 kD activities as the major components. Novel gamma-interferon showed a major activity peak with an estimated molecular weight of 52 kD and a minor activity peak of 28 kD. Thus, the activity profile (FIG. 4) and the silver stained protein profile (FIG. 3) of novel gamma-interferon are in good agreement with each other.

Over-estimation of the molecular size of glycoproteins by SDS-PAGE is a well-established phenomenon. The presence of carbohydrates interferes with and diminishes the amount of SDS bound per unit mass of polypeptide backbone. The diminished surface charge of the molecular complex results in a slower electrophoretic migration rate. For example, an apparent molecular weight of 160 kD was obtained by SDS-PAGE for an erythrocyte membrane glycoprotein which was estimated to be 31 kD by ultracentrifugal studies (Segrest, J. P. et al. *Biochem. Biophys. Res. Commun.*, 44:390–395, 1971).

Figure 5:
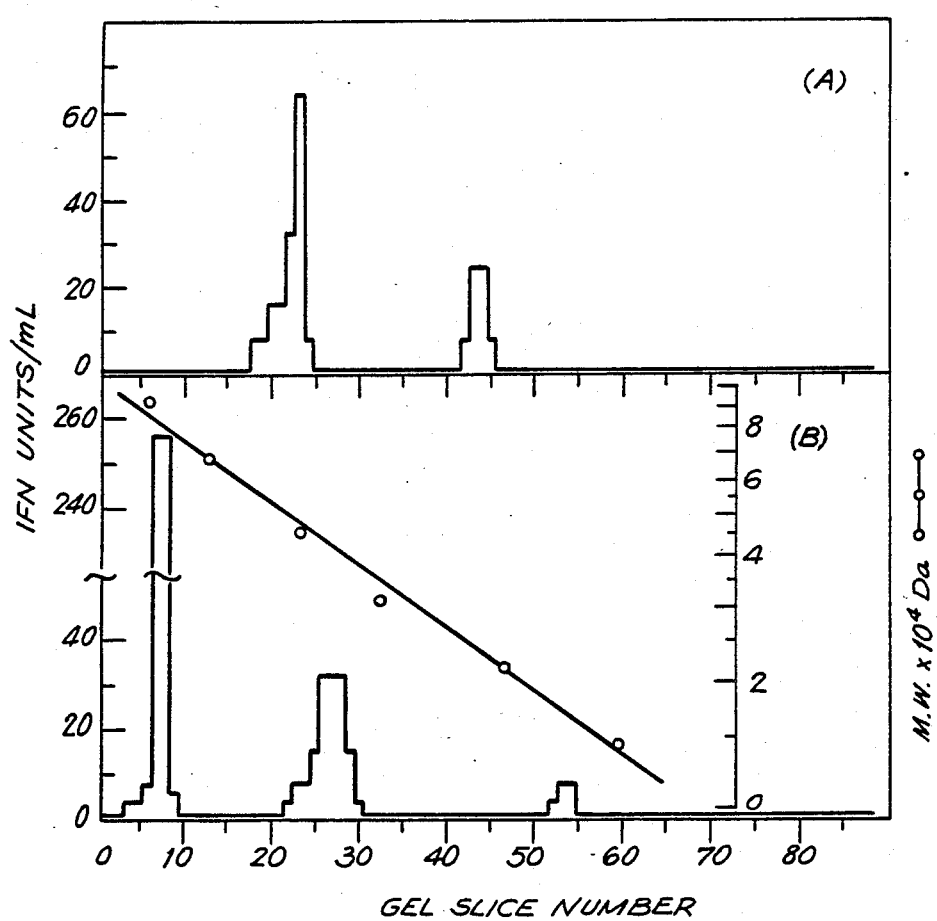
FIG. 5 is a graph of the activity profiles after SDS-PAGE of novel gamma-interferon before (A) and after (B) treatment with mixed glycosidases.

In order to correct the anomaly and to account for the discrepancy in the molecular weight estimates of 8 kD (determined by molecular-sieve chromatography) and 52 kD (determined by SDS-PAGE), the SDS-PAGE experiment was repeated after novel gamma-interferon had been treated with mixed glycosidases (obtained as a gift from K. Zoon, Office of Biologics Research and Review, FDA). Similar preparations of these mixed glycosidases were used by Knight and Fahey (*J. Interferon Res.*, 2:421-429, 1982) and Kelker et al. (*J. Biol. Chem.*, 258:8010-8013, 1983) to achieve apparently complete removal of carbohydrates from beta-interferon and gamma-interferon, respectively. FIG. 5 shows the activity profiles of novel gamma-interferon before (panel A) and after (panel B) treatment with mixed glycosidases. The treatment resulted in a shift in the molecular weight of the major component from 52 kD to 40 kD and of the minor component from 28 kD to 17 kD. Molecular weight estimates for novel gamma-interferon determined by SDS-PAGE varied between 50 and 53 kD. For simplicity, it is referred to as 52 kD. Based on experiments with classical gamma-interferon, the amount of enzyme used in this experiment should be in excess of the amount required for the complete removal of carbohydrates from novel gamma-interferon.

The 80 kD activity peak is apparently a component of the mixed glycosidases and not due to interferon activity from the induced culture. The mixed glycosidases preparation used in these experiments was found to contain a contaminant which exhibited an antiviral activity of about 2560 units per ml. It was resolved into a single activity peak of about 80 kD on SDS-PAGE.

Figure 6:
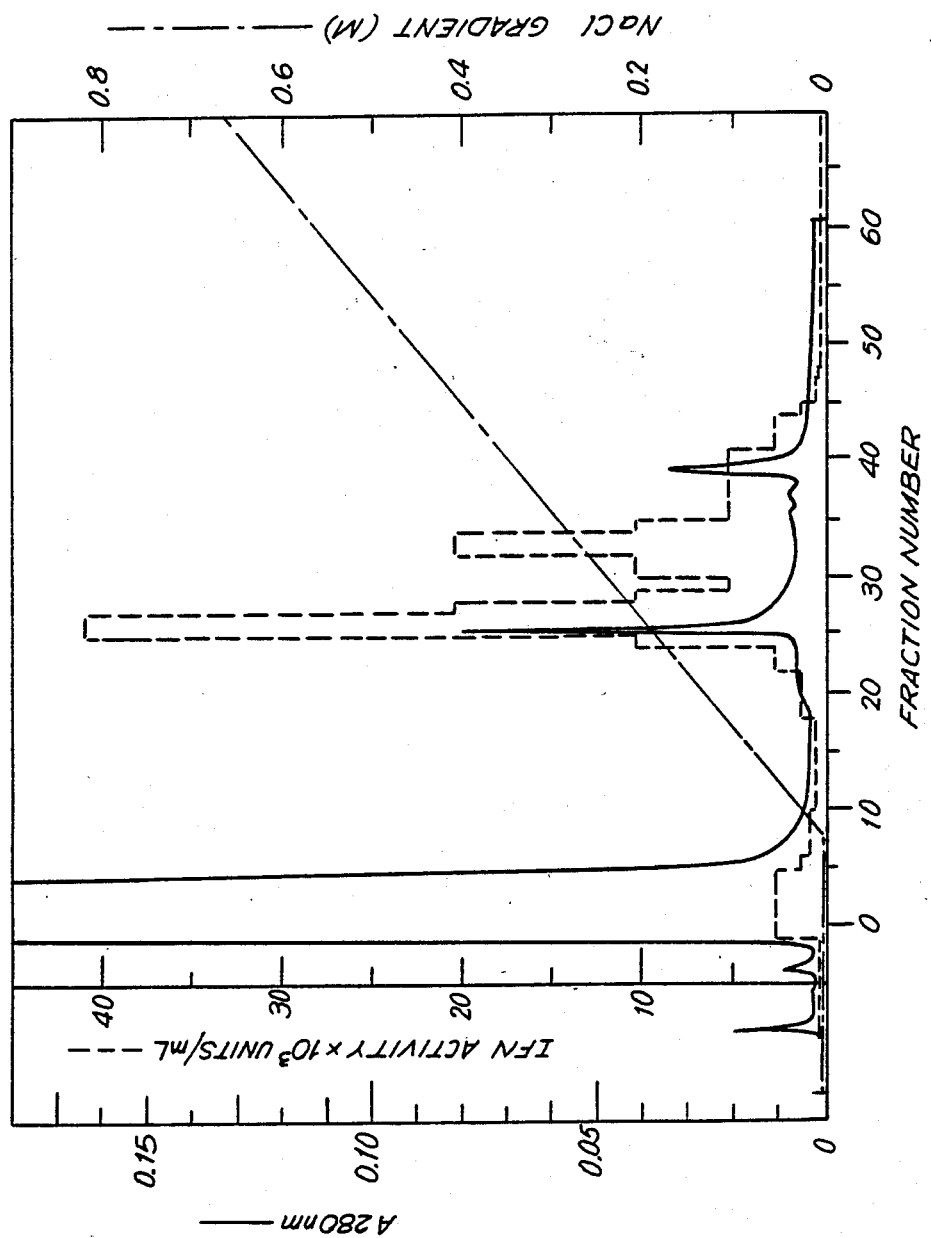
FIG. 6 is a graph of the elution profile of classical gamma-interferon from a cation exchange column.
Figure 7:
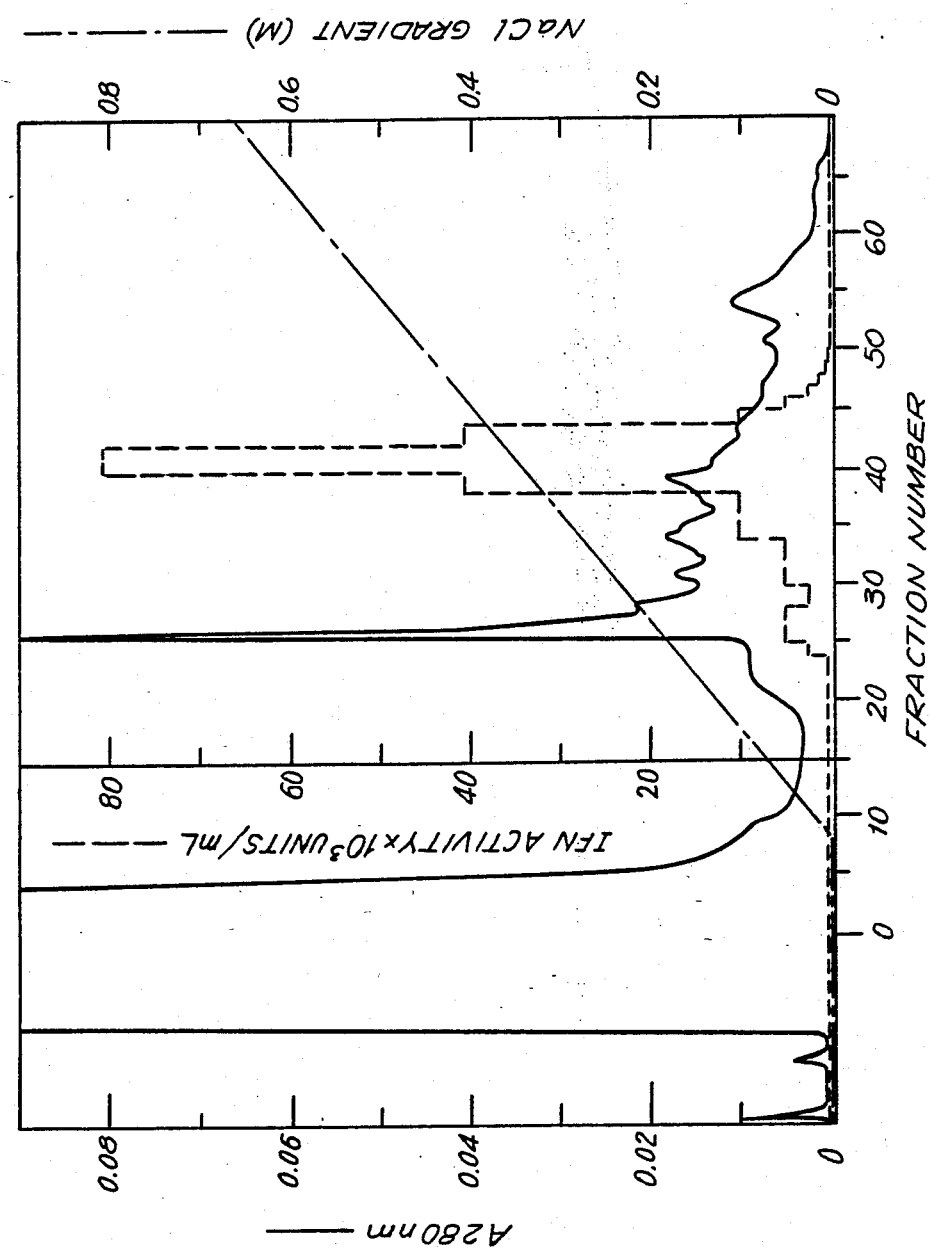
FIG. 7 is a graph of the elution profile of novel gamma-interferon from a cation exchange column.

D. Comparison of Electrostatic Charge Property By Ion-Exchange Chromatography. Typical elution profiles of classical and novel gamma-interferon on the cation exchange column are shown in FIGS. 6 and 7, respectively. Classical gamma-interferon was resolved into two major activity components, one eluting with 0.20 M NaCl and the other with 0.27 M NaCl (FIG. 6). Novel gamma-interferon on the other hand was resolved essentially into a single activity component eluting with 0.35 MNaCl (FIG. 7). The requirement of higher salt concentration for elution implies that the net electrostatic charge of novel gamma-interferon is higher than that of classical gamma-interferon at pH 7.5, a pH at which ion-exchange column chromatography was carried out. It follows then that the isoelectric point (pI) of novel gamma-interferon will necessarily be higher than that of classical gamma-interferon. The pI of classical gamma-interferon has been determined to be 8.6 by isoelectric focusing on polyacrylamide gels (Yip, Y. K. et al. *Proc. Natl. Acad. Sci. U.S.A.*, 78:1601-1605, 1981).

EXAMPLE 4

Activity and Reaction of Novel Gamma-Interferon

A. Cytotoxic Activities: In addition to the antiviral activity, classical gamma-interferon is known to exert direct and monocyte-mediated cytotoxic activities on tumor cells. Novel gamma-interferon was examined for its expression of these cytotoxic activities and compared with those of classical gamma-interferon on the basis of antiviral units.

The human colon adenocarcinoma cell line HT-29 (available as ATCC HTB 38, from American Type Culture Collection, Rockville, Md.) was used as target cell. Cultures of HT-29 cells were labelled with 5 uCi of $^{125}$I-iododeoxyuridine ($^{125}$IUdR; ICN Radiochemicals, Irvine, Calif.) in the presence of 3 $\mu$:M 5-fluorodeoxyuridine (Sigma Chemical Co., St. Louis, Mo.) to enhance the uptake of $^{125}$IUdR. After labelling for 24 hours at 37° C. in a humidified $CO_2$ incubator, the cells were washed 3× with complete medium (RPMI 1640 medium supplemented with 10% fetal bovine serum (FBS), 2 mM L-glutamine, 20 mM HEPES, and 50 $\mu$g/ml gentamycin). The labeled cells were then distributed in 96-well flat-bottomed plates at $1\times 10^4$ cells per 0.2 ml complete medium per well.

For the assay of direct cytotoxic activity, gamma-interferon samples at indicated concentrations were added in a volume of 50 $\mu$l per well. After incubation at 37° C. for 72 hours in a humidified $CO_2$ incubator, the plates were centrifuged and 100 $\mu$l of supernatant from each well was collected for determination of radioactivity in a gamma counter.

For the assay of monocyte-mediated cytotoxic activity, human monocytes were isolated by adherence on plastic culture wares as follows: Peripheral blood mononuclear cells were isolated from buffy coat cells of normal donors by fractionation on a Ficoll-Hypaque (Pharmacia Fine Chemicals, Piscataway, N.J.) gradient. Cells at the interphase were collected and washed 3× with complete medium, dispensed at approximately $3\times 10^6$ cells/ml in complete medium in plastic tissue culture flasks precoated with FBS for 1 hour at 4° C. After incubation at 37° C. for 2 hours, non-adherent cells were removed by discarding the culture medium. Adherent monocytes were washed gently 3× with complete medium, and then detached by incubation with PBS supplemented with 0.2% EDTA and 5% FBS at 4° C. for 30 minutes. The purified monocytes were added to the radio-labelled HT-29 cells at a ratio of 10:1, respectively, in a volume of 200$\mu$l of complete medium per well. The remaining steps were the same as described above for the assay of direct cytotoxic activity.

Cytotoxic activity (percent $^{125}$IUdR release) was calculated from the mean counts per minute of triplicate samples by the following formula:

Cytotoxic activity =

$$\frac{\text{Experimental minus Spontaneous release}}{\text{Total minus Spontaneous release}} \times 100$$

where total radioactivity incorporated was determined by lysis of the labelled HT-29 cells with 1% sodium dodecylsulfate. Spontaneous release of radioactivity was determined from supernatants of labelled HT-29 cells cultured in complete medium without monocytes or treatment with gamma-interferon. The results are presented below in Table 8.

TABLE 8

| Direct and Monocyte-Mediated Cytotoxic Activities of Human Gamma-Interferons | | | |
|---|---|---|---|
| | | Cytotoxicity (% $^{125}$IUDR Release) | |
| Gamma-Interferon Species | Interferon (Unit/ml) | Without Monocytes | Monocyte: HT-29 Cells (10:1) |
| None | — | 1.2 ± 0.9 | 24.2 ± 2.6 |
| 50 kD | 0.1 | 2.6 ± 1.9 | 28.0 ± 2.4 |
| (Classical) | 1.0 | 6.0 ± 0.6 | 31.8 ± 3.7 |
| | 10 | 11.5 ± 1.6 | 32.0 ± 2.8 |
| | 100 | 15.0 ± 3.4 | 31.0 ± 2.8 |
| 8 kD | 0.1 | 1.4 ± 1.2 | 27.4 ± 1.3 |
| (Novel) | 1.0 | 4.2 ± 0.4 | 25.2 ± 2.4 |
| | 10 | 8.2 ± 0.9 | 31.3 ± 1.9 |
| | 100 | 12.1 ± 1.3 | 35.4 ± 2.8 |

As can be seen from the results tabulated in Table 8, novel gamma-interferon, like classical gamma-interferon, demonstrated both direct and monocyte mediated cytotoxic activities on human colon adenocarcinoma cells. Both species of gamma-interferon showed substantially similar potency in these cytotoxic activities when compared on the basis of units of antiviral activity.

B. Antigenic Specificity: The three molecular weight species of interferon activity isolated by HPLC/molecular-sieve chromatography (see FIG. 1) were tested for their antigenic specificity by (i) neutralization of antiviral activity, and (ii) radioimmunoassay (RIA).

(i) Determination by Neutralization of Antiviral Activity: A predetermined amount of antiviral activity from the test samples was incubated with an excess of monoclonal antibody to human gamma-interferon or polyclonal goat anti-human interferon-alpha (commercially available from Interferon Sciences, Inc., New Brunswick, N.J.). Residual antiviral activity was assayed after incubation at 37° C. for 1 hr. Results are summarized in Table 9 below.

TABLE 9

Neutralzation of Interferon Activities Resolved on HPLC/ Molecular-Sieve Chromatography Under Nondenaturing Conditions Interferon (unit/ml) in the Presence of Antibody

| Sample | None | Polyclonal To alpha-interferon | Monoclonal To gamma-interferon |
|---|---|---|---|
| 50 kD gamma-interferon | 256 | 192 | <4 |
| 14.5 kD gamma-interferon | 96 | 128 | <4 |
| 8 kD gamma-interferon | 128 | 128 | <4 |
| alpha-interferon | 128 | <4 | 96 |

The above results show that the antiviral activity of all three molecular weight forms of interferon were neutralized completely by antibody to gamma-interferon but not by antibody to alpha-interferon.

(ii) Determination by RIA Method: The gamma-interferon RIA kit (Centocore, Malvern, Pa.) used in these experiments has been shown to be specific for human gamma-interferon (Chang, T. W. et al. Proc. Natl. Acad. Sci. U.S.A., 81:5219–5222, 1984). The assay was carried out by a procedure recommended by the manufacturer. Briefly, test samples were incubated with polystyrene beads coated with immobilized first antibody. After incubation at room temperature for 2 hrs., the beads were washed 3× with distilled water. The washed beads were then incubated with the recommended amount of a radioiodinated ($^{125}$I) second antibody at room temperature for 2 hrs. The beads were again washed 3× with distilled water to remove un bound reagent, the amount of bound second antibody was measured in a gamma counter. The results are summarized in Table 10 below.

TABLE 10

Binding of Resolved Interferon Species to Gamma-Interferon Specific Monoclonal Antibodies

| Sample | Interferon Units | Cpm Bound |
|---|---|---|
| Gamma-Interferon calibration standard | 0 | 276 |
| | 0.4 | 490 |
| | 4 | 1,920 |
| | 24 | 6,070 |
| | 45 | 10,305 |
| 50 kD | 20 | 26,035 |
| 14.5 kD | 25 | 18,115 |
| 8 kD | 12 | 16,360 |

The above results again confirm that all three molecular weight species of interferon isolated from the molecular sieve column are of the gamma type.

PAPER EXAMPLE 1

Sequence Comparison Between Novel and Classical Gamma-Interferon

The structural relationships between novel gamma-interferon and the 25 kD/20 kD classical gamma-interferon (subunits of the 50 kD gamma-interferon) will be established by comparing the amino acid sequences of these proteins, as follows:

Tryptic digestions will be performed in 0.5 percent ammonium bicarbonate, pH 8.5 (TPCK trypsin, Sigma Chemical Co., St., Louis, Mo.), at room temperature overnight using 2 percent (by weight) of enzyme with a second identical addition after the first 4 hours. The digestion will be performed on 30–40 micrograms of each species to be analyzed.

Tryptic peptides will be loaded onto an Altex ODS reverse phase High Performance Liquid Chromatography (HPLC) column (0.46×25 cm, Beckman Instruments Inc., Berkeley, Calif.) in 0.1 percent trifluoroacetic acid (TFA) in water, pH2, and eluted with a gradient of 0.1 percent TFA in water, pH2 and 0.1 percent TFA in acetonitrile. Peaks will be collected and analyzed by amino acid analysis and sequencing.

For amino acid composition analysis, samples will be hydrolyzed at 110° C. for 22 hours in evacuated Pyrex tubes, using 5.7 N HCl and analyzed using a Beckman 630D instrument.

Sequential Edman degradation (Edman, P. et al., Eur. J. Biochem 1:80–91. 1967) will be performed using a Beckman sequencer (Beckman Instruments Inc., Berkeley, Calif.), Model 890B. Peptides containing carbohydrate may not be resolved in a single peak using the above procedure, and can be further analyzed as in Rinderknecht, et al. (J. Biol. Chem. 259:6790–6797, 1984), incorporated by reference.

The present invention has been described in reference to preferred embodiments. It would be apparent to one of ordinary skill in the art that many additions, deletions or modifications could be made without departing from the scope of the invention, as claimed below.

What is claimed is:

1. A process for purifying a peptide having an amino acid sequence less than 100 amino acids, said peptide being immunochemically reactive with an antibody to gamma-interferon and having antiviral and cytolytic activities substantially the same as those of gamma-interferon, from an impure preparation comprising said peptide and also comprising gamma-interferon and other proteins as impurities; said process comprising the steps of:
   subjecting said preparation to adsorption onto silicic acid thereby causing said gamma-interferon and said peptide to bind to said silicic acid;
   desorbing said peptide and said gamma-interferon from said silicic acid;
   subjecting said desorbate to anion exchange chromatography, thereby causing impurities to bind to said column while said peptide and said gamma-interferon are excluded in a portion of the chromatographic effluent;
   subjecting said portion of said effluent to high-separation-speed molecular sieve chromatography under non-denaturing conditions thereby causing resolution of said gamma-interferon and said peptide;
recovering fractions containing said peptide;
subjecting said fractions containing said peptide to chromatography on a cation exchange residue, thereby causing said peptide to bind to said cation exchanger, and
eluting and recovering said peptide from said cation exchanger.

2. The process of claim 1 wherein said impure preparations containing said peptide are obtained from human leukocyte cells induced under gamma-interferon-producing conditions.

3. A process for purifying gamma-interferon from an impure preparation containing said gamma-interferon and other proteins as impurities, comprising the steps of:
subjecting said preparation containing said gamma-interferon to adsorption onto silicic acid;
desorbing said gamma-interferon;
subjecting said desorbate to anion exchange chromatography, thereby excluding said gamma-interferon in a portion of the chromatographic effluent;
subjecting said portion of said effluent to high-separation-speed molecular sieve chromatography under non-denaturing conditions thereby causing resolution of said gamma-interferon;
recovering fractions containing said gamma-interferon;
subjecting said fractions containing said gamma-interferon to chromatography on a cation exchanger, thereby causing said gamma-interferon to bind to said cation exchanger, and
eluting and recovering said gamma-interferon from said anion exchanger.

4. The process of claim 3 wherein said impure preparations containing said gamma-interferon are obtained from human leukocyte cells induced under gamma-interferon-producing conditions.

5. The process of claim 1, wherein said high-separation-speed molecular sieve chromatography is conducted on a highly-crosslinked agarose medium.

6. The process of claim 1, wherein said high-separation-speed molecular-sieve chromatography is conducted under a pressure of between about 125 and about 430 pounds per square inch.

7. The process of claim 6, wherein said pressure is about 225 pounds per square inch.

8. The process of claim 3, wherein said high-separation-speed molecular sieve chromatography is conducted on a highly-crosslinked agarose medium.

9. The process of claim 3, wherein said high-separation speed molecular sieve chromatography is conducted under a pressure of between about 125 and about 430 pounds per square inch.

10. The process of claim 9 wherein said pressure is about 225 pounds per square inch.

11. A process for purifying a peptide having an amino acid sequence less than 100 amino acids from an impure preparation containing said peptide, gamma-interferon, and other proteins as impurities, said peptide being immunochemically reactive with an antibody to gamma-interferon and having antiviral and cytoltic activities substantially the same as those of gamma-interferon, said process comprising the steps of:
(1) adsorbing said peptide and gamma-interferon on silicic acid from said impure preparation;
(2) removing said impurities from said adsorbed peptide and gamma-interferon by anion-exchange chromatography to form an impurity-free solution;
(3) exposing said impurity-free solution to high-separation-speed molecular sieve chromatography under non-denaturing conditions to form a peptide-containing solution free of gamma interferon; and
(4) recovering said peptide by cation-exchange chromatography.

* * * * *